United States Patent

Akerfeldt et al.

Patent Number: 5,423,824
Date of Patent: Jun. 13, 1995

[54] METHOD OF ACCESSING HARD TISSUE

[75] Inventors: Dan Akerfeldt; Gunnar Aström; Hakan Ahlström, all of Uppsala, Sweden

[73] Assignee: Radi Medical Systems AB, Uppsala, Sweden

[21] Appl. No.: 37,114

[22] Filed: Mar. 23, 1993

[30] Foreign Application Priority Data

Mar. 23, 1992 [SE] Sweden ................... 9200893

[51] Int. Cl.6 .................................... A61B 17/16
[52] U.S. Cl. ........................ 606/80; 606/180; 128/754
[58] Field of Search ............... 606/80, 180, 185; 128/751, 753, 754

[56] References Cited

U.S. PATENT DOCUMENTS

| | | | |
|---|---|---|---|
| 1,630,239 | 5/1927 | Binkley et al. | 606/180 |
| 1,677,337 | 7/1928 | Grove | 606/180 |
| 1,867,624 | 7/1932 | Hoffman | 128/754 |
| 3,071,201 | 1/1963 | Phipps | 175/410 |
| 3,128,836 | 4/1964 | Hjalsten et al. | 175/408 |
| 3,628,524 | 12/1971 | Jamshidi | 128/2 B |
| 3,827,331 | 8/1974 | Muenchinger | 85/41 |
| 3,861,477 | 1/1975 | Lazayres | 175/227 |
| 4,142,517 | 3/1979 | Stavropoulos et al. | 128/754 |
| 4,220,213 | 8/1980 | Hamilton | 175/45 |
| 4,267,893 | 5/1981 | Mannon, Jr. | 175/65 |
| 4,306,570 | 12/1981 | Matthews | 128/754 |
| 4,319,649 | 3/1982 | Jeter | 175/73 |
| 4,325,438 | 4/1982 | Zuvela | 175/50 |
| 4,365,444 | 12/1982 | Chwae | 51/94 |
| 4,428,441 | 1/1984 | Dellinger | 175/61 |
| 4,441,839 | 4/1984 | Baduel et al. | 405/202 |
| 4,442,908 | 4/1984 | Steenbock | 175/74 |
| 4,513,754 | 4/1985 | Lee | 128/753 |
| 4,541,423 | 9/1985 | Barber | 606/80 |
| 4,543,966 | 10/1985 | Islam et al. | 128/754 |
| 4,567,954 | 2/1986 | Voight, III et al. | 175/422 |
| 4,635,738 | 1/1987 | Schillinger et al. | 175/398 |
| 4,638,873 | 1/1987 | Welborn | 175/73 |
| 4,696,308 | 9/1987 | Meller et al. | 128/754 |
| 4,699,224 | 10/1987 | Burton | 175/61 |
| 4,739,843 | 4/1988 | Burton | 175/73 |
| 4,785,894 | 11/1988 | David, Jr. et al. | 175/39 |
| 4,878,794 | 11/1989 | Potucek | 411/395 |
| 4,880,066 | 11/1989 | Steiginga et al. | 175/75 |
| 4,919,146 | 4/1990 | Rhinehart et al. | 128/752 |
| 4,943,236 | 7/1990 | Linkow et al. | 433/165 |
| 5,009,271 | 4/1991 | Maric et al. | 175/53 |
| 5,018,530 | 5/1991 | Rank et al. | 128/754 |
| 5,062,845 | 11/1991 | Kuslich et al. | 606/80 |
| 5,074,366 | 12/1991 | Karlsson et al. | 175/76 |

FOREIGN PATENT DOCUMENTS

| | | | |
|---|---|---|---|
| 832433 | of 0000 | Belgium . | |
| 0296421 | 6/1988 | European Pat. Off. | A61B 10/00 |
| 2544375 | 10/1984 | France . | |
| 130318 | of 0000 | German Dem. Rep. . | |
| 2636102 | 12/1977 | Germany | B23B 41/00 |
| 2839868 | 4/1979 | Germany | E21C 23/00 |
| 3318204 | 3/1984 | Germany | B23B 51/02 |
| 3644490 | 7/1988 | Germany | A61B 10/00 |
| 2080367 | 2/1982 | United Kingdom | E21B 7/06 |
| 401360 | 2/1974 | U.S.S.R. | 128/754 |
| 1306571 | 4/1987 | U.S.S.R. . | |

Primary Examiner—Michael H. Thaler
Attorney, Agent, or Firm—Foley & Lardner

[57] ABSTRACT

A device for puncturing cortical bone. The device consists of a cannula and inside of it an axially movable needle. The distal end of the needle has an eccentrically shaped tip which, by drilling, forms a hole, larger than the outer diameter of the needle, through corticalis, whereupon the enclosing cannula can be inserted into the drilled hole. In this way the cannula's position in the bone is secured and the cannula functions as a fixed anchored guiding channel for further sampling or treatment.

5 Claims, 2 Drawing Sheets

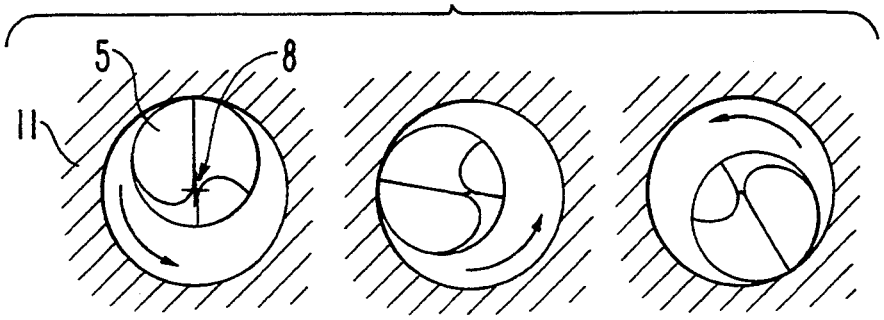
FIG. 6
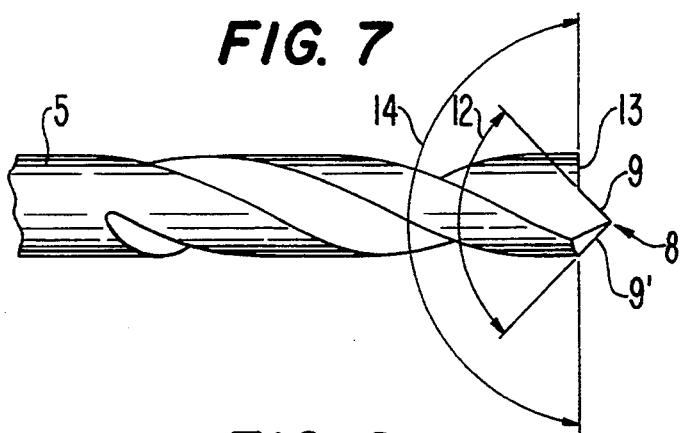
FIG. 7
FIG. 8
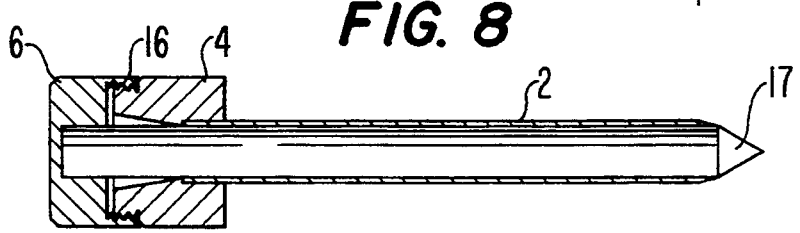
FIG. 9
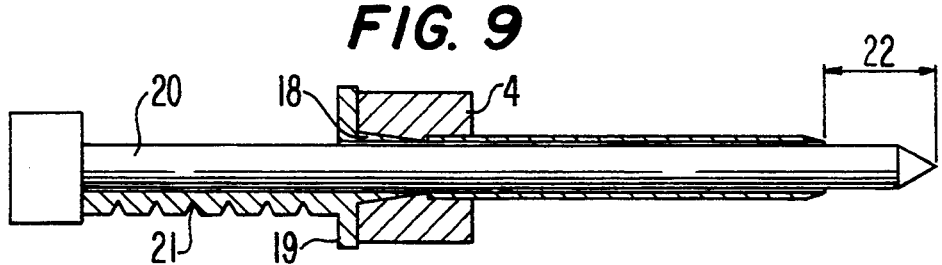
FIG. 10
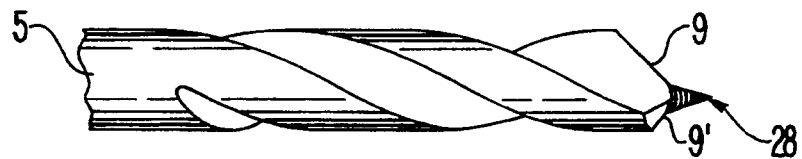

METHOD OF ACCESSING HARD TISSUE

BACKGROUND OF THE INVENTION

1. Field of the Invention

The present invention primarily relates to a device for puncturing hard tissue in, for example, humans or animals, and to a technique for puncturing in this type of tissue.

The skeleton is the site of many different pathological lesions, blood diseases etc. The lesions are often visible on X-rays of the skeleton, but in general, it is not possible, using X-ray, to determine the cause of the lesion. In order to with certainty determine the nature of the lesion, parts of the bone must be removed and examined under microscope.

Biopsy sampling of the bone is difficult to perform due to the fact that the lesion is often surrounded by the hard outer surface of the bone known as corticalis.

2. Discussion of the Related Art

One way to gain access to the lesion through the cortical bone is to introduce a conventional spiral drill equipped with a cannula, drill through the cortical bone, then remove the drill. The cannula remains in place in the soft tissue, but cannot be inserted through the drilled hole in the cortical bone because the outer diameter of the cannula is larger than the diameter of the drilled hole. The disadvantage is that the cannula can easily be moved out of position, making it difficult to relocate the drilled hole in order to, for example, introduce a biopsy needle. This disadvantage is especially apparent when performing a puncture not at a right angle to the bone surface.

Currently, two main methods are used to obtain biopsy samples of bone: operative biopsy and percutaneous needle biopsy. An operative procedure often yields good results but requires general anesthesia as well as substantial resources and cost. Percutaneous needle biopsy is performed under a local anaesthetic. The needle usually consists of a sharpened or saw-toothed sampling cannula which is introduced into the lesion resulting in the excision of a biopsy sample. Upon introduction, a stylet is inserted into the cannula forming a sharp distal tip in order to facilitate entry into the soft tissue. Examples of this type of needle are described in European Pat. No. 0,296,421 (the Ostycut needle) and in U.S. Pat. No. 3,628,524 (the Jamshidi needle).

Existing needle biopsy methods have the substantial disadvantage of not being able to easily penetrate cortical bone. Common biopsy needles such as, for example, Jamshidi and Ostycut all have a needle tip which can only penetrate thin or soft cortical bone. This is due to the fact that the tip does not clear away the material like a drill, but instead wedges itself in using considerable insertion force combined with rotation. A further disadvantage is that the substantial friction which results between the needle and the cortical bone hinders the manipulation of the needle towards the target and causes development of heat which can be painful to the patient. Also common are needle types in which the distal end of the cannula is saw-toothed. Examples of this type of needle are described in U.S. Pat. No. 4,306,570 (the Corb needle). The disadvantage of the saw-teeth, however, is that the teeth become plugged with drill chips when the depth of the cut exceeds the length of the teeth.

Furthermore, the saw-teeth must be covered by an outer protective cannula upon insertion into the soft tissue of the body in order to avoid damage. This increases the requisite outer diameter of the needle.

Drills and drill units for making holes having a greater diameter than the diameter of the drill itself are as such, already in existence (see, for example, U.S. Pat. Nos. 4,635,738, 4,878,794, 5,009,271). These patents concern primarily drilling in the earth, for example, for oil, and lie therefore outside the technical area dealt with by the present invention.

SUMMARY OF THE INVENTION

Therefore, there is a need for a device or method to puncture hard tissue in which the drill can be removed while the cannula remains in place.

There is also a need for a device or method to puncture hard tissue for use in performing a puncture not at a right angle to the bone.

There is further a need for a needle biopsy device and method which can also penetrate hard tissue such as cortical bone.

Another need is for a device and method to puncture hard tissue which clears away the material.

Yet another need is for a device and method to puncture hard tissue which is less painful to the patient.

The present invention (henceforth called "the puncture instrument"), which is defined in the attached claims, eliminates the disadvantages that occur with the known biopsy methods described above.

According to one aspect of the invention, there is provided a device for puncturing hard tissue in humans or animals. The apparatus includes a cannula, with a distal end and a proximal end, forming a void. A needle with a distal end and a proximal end is removably and rotatably inserted with the void. The distal end of the needle may extend from the distal end of the cannula. A tip is disposed on the distal end of the needle, with a radial displacement in relation to an axial center of the needle.

In one preferred embodiment, the needle is shaped like a spiral drill having one or more drill cutters.

In another preferred embodiment, the needle is equipped with a tip which is radially displaced from the geometrical central axle of the needle, and the tip includes a point angle formed by the drill cutters.

In another aspect, the invention is manifested as a method for accessing hard tissue in humans or animals.

According to the method, the soft tissue around the hard tissue is punctured by a needle inserted within a cannula. The needle drills a hole with a diameter larger than the diameter of the cannula in the hard tissue. The cannula is inserted into the hole. The needle is removed.

BRIEF DESCRIPTION OF THE DRAWINGS

The invention will now be described in more detail below, with reference to the attached drawings, in which:

FIG. 6 is a schematic drawing which describes the wobbling function of the drill during use;

FIG. 7 is a longitudinal view of an alternative embodiment of a drill tip;

FIG. 8 is a longitudinal view of the instrument equipped with a needle having a smooth tip as well as an alternative embodiment of the handle;

FIG. 9 is a longitudinal view which shows a depth-stop; and

FIG. 10 shows an alternative embodiment of the drill's tip.

DETAILED DESCRIPTION OF THE PREFERRED EMBODIMENTS

Figure 1:
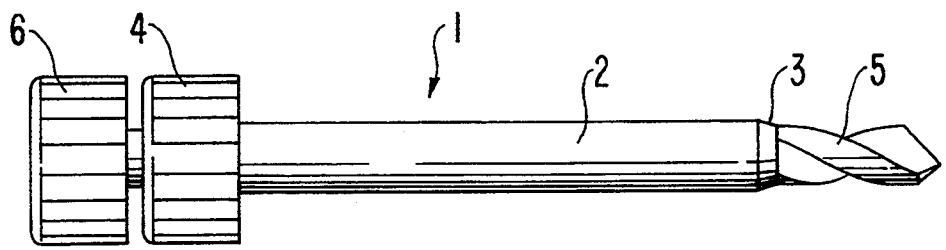
FIG. 1 is a schematic longitudinal view of the puncture instrument in accordance with the invention.

The puncture instrument 1 in accordance with the invention, shown in FIG. 1 consists of a cannula 2, the distal end 3 of which is externally tapered 3'. Around the cannula's proximal end 4 a handle 4' is attached. Fitted into the cannula is an axially movable solid needle 5 or stylet. Around the needle's 5 proximal end 6, a handle 6' is attached.

Figure 2:
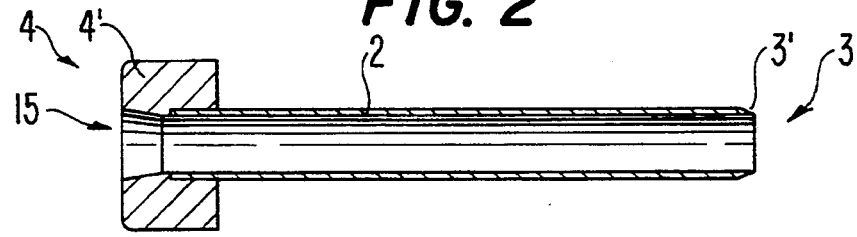
FIG. 2 is a longitudinal section through the cannula of the instrument.

FIG. 2 shows a longitudinal section through the cannula. Preferably, the cannula has an outer diameter of 2 mm, an inner diameter of 1.6 mm and a total length of approximately 120 mm, but the dimensions may vary within broad limits for special applications. The distal end 3 of the cannula 2 is externally tapered to a sharp edge 3'. The handle 4' on the cannula is equipped with an internal taper 15 so that a syringe with a luer-attachment can be connected, for example, for aspiration or injection.

Figure 3:
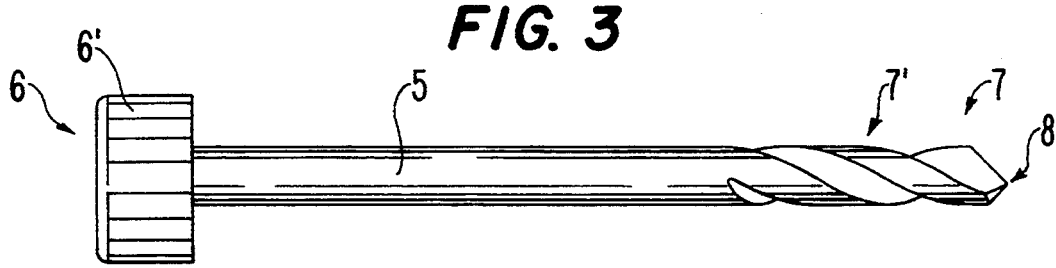
FIG. 3 is a longitudinal view of an embodiment of the instrument's needle.

FIG. 3 shows a longitudinal view of a first embodiment of the solid needle. Approximately 10 mm of the needle's distal end 7 is shaped like a spiral drill 7'. Preferably, the needle has an outer diameter of 1.6 mm. The length of the needle is proportioned so that the drill tip extends approximately 5 mm out from the distal end 7 of the cannula in assembled condition, so that the drill's discharge of chips is not inhibited by the cannula. The needle's dimensions can, obviously, also vary according to application.

Figure 4:
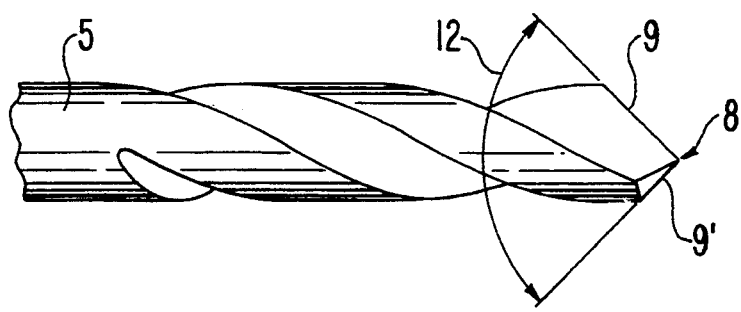
FIG. 4 is a longitudinal view of the embodiment's drill tip rendered in FIG. 3.

FIG. 4 shows a longitudinal view of the needle's tip in another embodiment, in which the tip is shaped like a conventional spiral drill with two drill cutters 9, 9', but the difference is that the tip 8 formed by the drill cutters does not, as is the normal case, coincide with the geometrical center axis of the needle. Preferably, the needle has an outer diameter of 1.6 mm and the drill tip is displaced approximately 0.3 mm relative to the needle's center axis. In this example, however, the long cutter 9 has a radius of 1.1 mm and the short cutter 9' a radius of 0.5 mm. The drill tip's point angle 12 is preferably 80 degrees. The greater angle reduces the ability of the drill to enter bone during oblique punctures and a smaller angle increases the drill's requisite insertion force.

Figure 5:
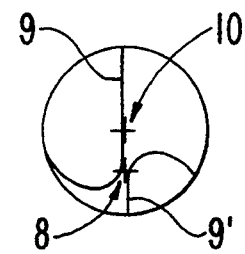
FIG. 5 is an end view of the drill tip.

FIG. 5 shows an end view of the needle's drill tip. The needle's geometrical center of rotation is marked 10 and the position of the drill tip is marked 8.

FIG. 6 shows schematically how the needle's drill tip works. When drilling into bone 11 the drill tip 8 functions as a guide and forces the drill to "wobble" around in the hole with the drill tip as the center of rotation. In this way, the drilled hole is given a radius which is equivalent to the radius of the longest drill cutter 9. Consequently, the diameter of the hole will be 2.2 mm if the radius of the longest drill cutter is 1.1 mm.

FIG. 7 shows an alternative embodiment of the needle's drill tip. In this embodiment, the outer part 13 of the long cutter 9 has a greater point angle 14, preferably 180 degrees. This gives the advantage that the drill's requisite insertion force is reduced, while at the same time the drill tip's point angle 12, which is 80 degrees, still facilitates entry into the bone during oblique punctures The handles 4' 6' on the cannula 2 and the respective needle 5 are preferably made of plastic and equipped with external grooves (not shown) which provide a good grip for manual rotation and also function as driving slots when the instrument is assembled into a drill chuck.

If a drill is used, it is preferably electrically or pneumatically powered. Electrical battery power is preferable due to the easy manageability since no connecting cord is necessary. Suitable axle rotation speed is 100–300 rpm. The drill can also be manually operated, e.g., using a gear wheel equipped with a crank. The manual drive is simple in design but a disadvantage is that the needle is easily jarred out of place during cranking.

Dental-type drill machines are also possible alternatives.

The needle tip is preferably made by grinding a solid piece of wire. The spiral shaped grooves in the tip are cut by moving the wire axially under a grinding disc while at the same time rotating the needle with the desired tip 8 as the axle of rotation. The relationship between the axial feeding of the needle and the rotation is adjusted so that the intended spiral angle is obtained. The axial surfaces on the tip are cut with clearance behind the cutting edges as in a conventional spiral drill.

An alternative embodiment shown in FIG. 10 of the needle is that the drill tips 8 is formed like a taper with external spiral threads, and the drill cutters 9 join the base of the taper. When drilling, the taper's threads help to feed the drill forward and reduce the insertion force required.

The drill tip can also be truncated and equipped with a small transverse edge. This reduces the drill's requisite insertion force, but the disadvantage is that it is more difficult for the tip to enter the bone during oblique punctures.

Another alternative embodiment is that the drill tip 8 is displaced corresponding to the radius of the whole needle, that is, the tip coincides with the needle's circumference or outer diameter. The drill tip then consists of a single long drill cutter, and the drill therefore will fill a hole equivalent to double the size of the needle's diameter.

The handle 4' on the cannula 2 is equipped with an internal taper 15 so that a syringe with a luer connector can be attached for aspiration or injection.

FIG. 8 shows an alternative embodiment where the handle is made with a threaded 16 or bayonet connection (not shown) so that the cannula 2 and the needle 5 can be locked relative to one another in order to simplify the handling during insertion and drilling. In this example the needle has a smooth tip 17 meant to be able to replace the drill-shaped needle during puncture of skin and soft tissue.

FIG. 9 shows a depth-stop 19. During sampling through the cannula, it is of value to be able to limit how deep the sampling needle 20 shall be inserted relative to the cannula 22, so that the puncture will be made only up to the depth desired. The depth-stop consists of a pin with a number of kerfs (or fractural impressions) 21 equally distributed, preferably made of plastic so that the pin 21 can easily be broken off at any kerf to the desired length and in this way functions as a depth-stop for, for example, a biopsy needle.

In order to puncture cortical bone for sampling or treatment of a lesion, the puncture instrument is used preferably in the following way:

The instrument is inserted, assembled in accordance with FIG. 1, into the soft tissue towards the cortical bone surface. If the insertion is made through sensitive areas, for example, near nerve pathways, the needle drill 5 can be replaced during insertion by a needle 17 that has a smooth tapered tip as shown in FIG. 8, and when the soft tissue has been penetrated the needle 17 is exchanged for a needle drill 5 as described in the invention. When the drill tip has reached the bone surface, the drill is rotated manually or using a machine (not shown), and the drill is allowed to work its way through the hard cortical bone to the desired depth. As described in FIG. 6, the drill then occupies a hole which is larger than the outer diameter of the cannula, allowing the cannula along with the drill to easily enter the drilled hole, whereupon the drill can be removed with the instrument's cannula remaining in the bone. In this simple and expeditious way, the cannula has now been positioned like a fixed anchored guiding channel from the skin surface in through the corticalis to the lesion for further sampling or treatment.

A considerable advantage with this method is that with the cannula in a fixed position as a guiding channel, repeated biopsies can be performed in a simple way through the cannula. Various types of lesions require different types of biopsy needles in order to provide a satisfactory sample for analysis. Therefore it is of value, in instances of poor sample yield, to be able to change to a new type of biopsy needle and immediately take a new sample.

Described here have been, primarily, the advantages of the puncture instrument in relation to biopsy sampling, but in addition, it is also suitable for all types of radiological interventions or orthopedic-surgical procedures which require access to the bone through the corticalis. Administration of drugs and other substances can also be carried out in a simple way using the invention.

While specific embodiments of the invention have been described and illustrated, it will be clear that variations in the details of the embodiments specifically illustrated and described may be made without departing from the true spirit and scope of the invention as defined in the appended claims.

What is claimed is:

1. A method of accessing hard tissue in humans or animals, comprising the steps of:
    (a) puncturing a soft tissue around the hard tissue by a first needle inserted within a cannula;
    (b) drilling a hole having a diameter larger than the diameter of the cannula in the hard tissue with a second needle, wherein the drilling includes rotating the second needle with a drill point having a radial displacement in relation to an axial center of the second needle;
    (c) inserting the cannula into the hole; and
    (d) removing the second needle.

2. A method as in claim 1, further comprising the steps of:
    (a) initially inserting the first needle with a smooth tapered tip into the cannula;
    (b) after the puncturing step, removing the first needle with the smooth tapered tip from the cannula; and
    (c) inserting the second needle with the drill point into the cannula, prior to the drilling step.

3. A method as in claim 1, wherein the drilling step comprises rotating the second needle manually.

4. A method as in claim 1, wherein the drilling step comprises rotating the second needle by a machine.

5. A method as in claim 1, further comprising the step of accessing a portion of the hard tissue through the cannula, after the removing step.

* * * * *